United States Patent
Simon et al.

(10) Patent No.: US 8,150,494 B2
(45) Date of Patent: Apr. 3, 2012

(54) APPARATUS FOR REGISTERING A PHYSICAL SPACE TO IMAGE SPACE

(75) Inventors: David Simon, Boulder, CO (US); Amir Ghanei, Louisville, CO (US); Kevin Mark, Westminster, CO (US); Andrew Lajoie, Superior, CO (US); Geoffrey M. Ruckel, Denver, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 1374 days.

(21) Appl. No.: 11/693,558

(22) Filed: Mar. 29, 2007

(65) Prior Publication Data

US 2008/0242978 A1   Oct. 2, 2008

(51) Int. Cl.
*A16B 5/05* (2006.01)

(52) U.S. Cl. ............ 600/414; 600/424; 600/426

(58) Field of Classification Search ............ 600/407, 600/410, 414, 424, 425, 426; 382/128, 131
See application file for complete search history.

(56) References Cited

U.S. PATENT DOCUMENTS

| | | | |
|---|---|---|---|
| 5,592,939 A | 1/1997 | Martinelli | |
| 5,740,808 A | 4/1998 | Panescu et al. | |
| 5,769,789 A | 6/1998 | Wang et al. | |
| 5,799,099 A | 8/1998 | Wang et al. | |
| 5,913,820 A | 6/1999 | Bladen et al. | |
| 5,983,126 A | 11/1999 | Wittkampf et al. | |
| 6,052,477 A * | 4/2000 | Wang et al. | 382/131 |
| 6,381,485 B1 | 4/2002 | Hunter et al. | |
| 6,474,341 B1 | 11/2002 | Hunter et al. | |
| 6,640,127 B1 | 10/2003 | Kosaka et al. | |
| 2004/0002642 A1 | 1/2004 | Dekel et al. | |
| 2004/0019274 A1* | 1/2004 | Galloway et al. | 600/425 |
| 2004/0167391 A1* | 8/2004 | Solar et al. | 600/411 |
| 2004/0215071 A1 | 10/2004 | Frank et al. | |
| 2005/0085714 A1 | 4/2005 | Foley et al. | |
| 2005/0085720 A1 | 4/2005 | Jascob et al. | |
| 2006/0084867 A1 | 4/2006 | Tremblay et al. | |
| 2006/0098851 A1* | 5/2006 | Shoham et al. | 382/128 |

FOREIGN PATENT DOCUMENTS

WO   WO-2004070655   8/2004

OTHER PUBLICATIONS

International Search Report and Written Opinion for PCT/US2008/004085 mailed Oct. 20, 2008 claiming benefit of the current case, U.S. Appl. No. 11/693,558, filed Mar. 29, 2007.
International Preliminary Report on Patentability and Written Opinion for PCT/US2008/004085 mailed Oct. 8, 2009 claiming benefit of the current case, U.S. Appl. No. 11/693,558, filed Mar. 29, 2007.

* cited by examiner

*Primary Examiner* — Brian Casler
*Assistant Examiner* — Christopher Cook
(74) *Attorney, Agent, or Firm* — Harness, Dickey

(57) ABSTRACT

A method and apparatus for registering physical space to image space is disclosed. The system allows for determining fiducial markers as pixels or voxels in image data. The system can correlate and register the determined fiducial points with fiducial markers in physical space.

23 Claims, 5 Drawing Sheets

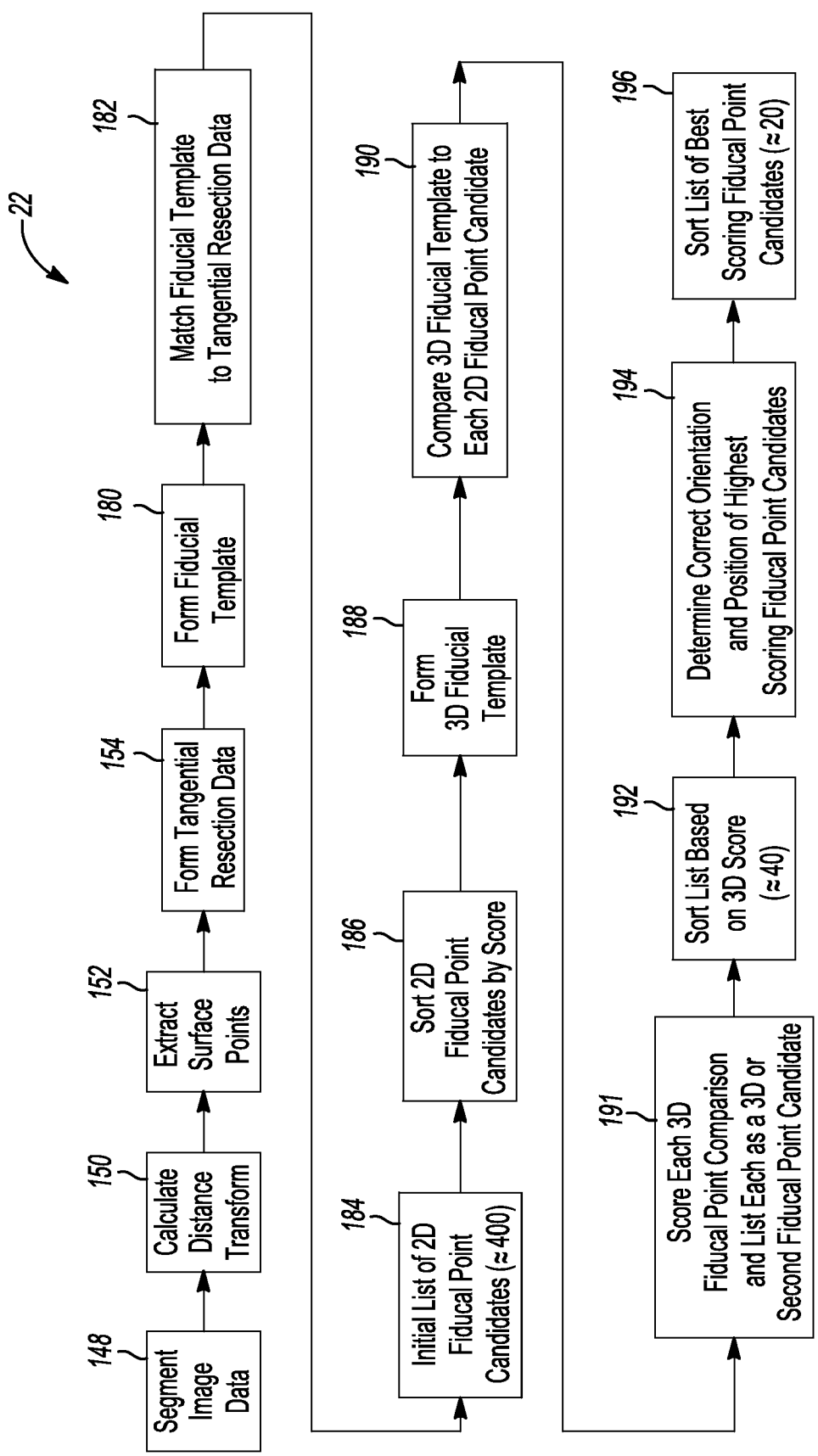

APPARATUS FOR REGISTERING A PHYSICAL SPACE TO IMAGE SPACE

FIELD

The present disclosure relates to a method and apparatus for performing a computer assisted surgical procedure, and particularly to a method and apparatus for registering physical space to image space.

BACKGROUND

The statements in this section merely provide background information related to the present disclosure and may not constitute prior art.

Surgical procedures can be performed on anatomies, such as the human anatomy for providing a therapy to the anatomy. Therapies can include implantation of prosthesis, applications of pharmaceutical or biological materials, and other therapies. To apply a therapy to the internal portions of the anatomy, however, an incision or axis portal is generally required to be formed in the anatomy.

The axis portal, such as an incision, can require healing and recovery time in addition to the reason for the application of the therapy. Therefore, it is desirable, to minimize the trauma produced by and the size of the axis portal. In reducing the size of the axis portal, however, the ability of a user, such as a surgeon, to effectively apply a therapy can be reduced. Therefore, it is desirable to provide a mechanism so that a surgeon can provide a therapy without minimization or reduction of effectiveness of the physical or in viewing the area to apply a therapy. Navigation of instruments relative to an anatomy can be used. The navigation can use acquired image data to confirm and position an instrument relative to the patient. The image data, if it is preacquired or acquired prior to positioning an instrument with an anatomy, is generally registered to the patient. The registration process, however, can require several steps and interaction of a user with a workstation or computer system. Therefore, it is desirable, to minimize the steps of a user to register image data to a patient and to allow the registration process to be efficient as possible.

SUMMARY

A system and apparatus is disclosed to allow for registration of image space to physical space. The physical space can include patient space or the navigated space relative to a patient. The physical space can include any portion or the entire patient or area surrounding the patient. Generally patient space includes that area which is part of the navigable field in which an instrument or navigated portion can be tracked.

Image space can be image data acquired of any appropriate portion, such as image data of a patient. The image data can be any compilation or data set of image points that is imaged with any appropriate imaging system. The image points can include pixels, voxels, groups of pixels or voxels, or any other appropriate data point. The image data can include data regarding the anatomy of the patient, a physical property of a portion affixed relative to the patient, and other appropriate data. For example, the patient may also include a fiducial point or marker. The fiducial point or marker can be a natural portion of a patient or can include an artificial structure that is interconnected to the patient. For example, a fiducial marker can be stuck to the surface of the patient using an adhesive material. The image data can then include image points or data points about the patient and the fiducial marker.

According to various embodiments a method of registering image space and physical space in a computer aided surgical navigation system is disclosed. The method can include acquiring image data to define the image space including a plurality of points having a sub-plurality of fiducial points. The method can further include forming a template of a fiducial marker, comparing the template to the plurality of points, and determining the sub-plurality of fiducial points from the plurality of points based on the comparing the template. Fiducial markers in the physical space can be identified. A first subset of the fiducial points can be matched with a first subset of the fiducial markers and a transformation of the image space to the physical space can be made with the match. Image space can also be registered to the physical space.

According to various embodiments a method of registering image space and physical space in a computer aided surgical navigation system is disclosed. The method can include imaging a member including a fiducial marker affixed to the member to acquire image data and comparing a computer readable fiducial template to the image data to identify fiducial points in the image data. A device defining a single center point in any orientation can be tracked relative to the fiducial marker and a position of the fiducial marker can be determined based on tracking the device. The identified fiducial points and the determined fiducial markers can be compared and the image space can be registered to the physical space.

According to various embodiments a computer aided surgical navigation system to navigate a procedure relative to a patient having registration of image space and physical space is disclosed. The system can include a tracking system having a localizer and a tracking device. A fiducial marker can be associated with the patient to define a fiducial marker point. An instrument can be associated with the tracking device, wherein the instrument includes a fiducial marker contact portion defining a single center point. A processor can be associated with the tracking system to determine a position of the single center point in physical space. A memory system can store the image data of the patient and the fiducial marker and a display device can display the image data. The processor can execute a first set of instructions to compare the image data of the patient and the fiducial marker to a predetermined fiducial template to determine fiducial points in the image data. The processor can also execute a second set of instructions to match the fiducial points in image space to fiducial marker points in physical space.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 4 is a detailed flow diagram of a portion of the process illustrated in FIG. 1;

DETAILED DESCRIPTION

The following description is merely exemplary in nature and is not intended to limit the present disclosure, application, or uses. Initially, one skilled in the art will understand that the system and apparatus disclosed herein can be used in any appropriate procedure. Although a head frame is illustrated attached to a cranium and image data is illustrated for a cranium, and appropriate portion of the anatomy can be imaged. Moreover, a head frame may not be necessary and a dynamic reference frame can be attached to any appropriate structure, such as a bone screw, an adhesive base, an orifice, etc.

Figure 1:
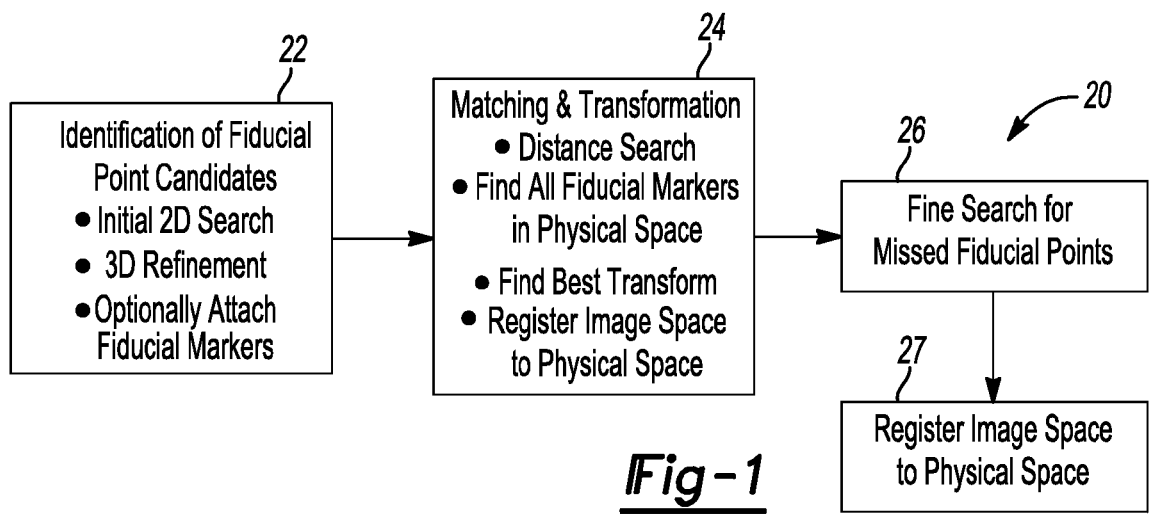
FIG. 1 is a schematic overview of a system for identification of fiducial points in image data and registration to physical space, according to various embodiments.

With reference to FIG. 1, an identification and registration system 20 to identify a fiducial point in image data and registering the identified or determined fiducial point to a fiducial marker in physical space or patient space. Herein, patient space can be understood to be a specific physical space to which registration can be made. Discussed in detail herein, registration matches or correlates points in the image space and points in the physical space. Image data can be acquired in any appropriate format, as discussed herein. The image data can be used during an operative procedure, prior to an operative procedure, or after an operative procedure.

With continuing reference to FIG. 1, the system 20 includes three main portions or procedures. Initially fiducial points in image data defining image space are identified in block 22. Once fiducial points are identified in block 22, a matching and registration process occurs in block 24. After the matching and transformation process in block 24, a fine or refinement search can be optionally performed in block 26. After the fine search, if needed, in block 26 a final transformation or registration can occur in block 27. The registration can register the image space and the patient space based upon the matched fiducial markers and fiducial points.

The initial identification of the fiducial points in block 22 can include two main sub-portions. The sub-portions can include an initial two-dimensional (2D) search. In the 2D search the fiducial points can be searched in a 2D resected data set or after a 2D resection of three-dimensional (3D) data. After the initial 2D search, 3D refinement search can occur. The 3D refinement search can occur in a three dimensional image data. As is understood in the art, two dimensional image data and three dimensional image data can be acquired with a single imaging process. For example, a plurality of two dimensional image slices can be registered together or stacked to create a three dimensional model. The 3D refinement search can then search the created three dimensional model at the locations identified in the initial two dimensional search. In addition, as discussed herein, 2D image data can be resected from the 3D data set for the 2D search.

After the search and identification of the fiducials points in block 22, a match and transformation can occur in block 24. Briefly, the matching and transformation can include finding or determining all or a subset of the fiducial markers in physical space. The finding or determining of the fiducial markers in patient space or physical space can occur according to any appropriate method, as discussed further herein. Once the fiducial markers are determined in physical space they can be compared to the determined fiducial points in the image space, identified or determined in block 22. Initially a distance search can be performed for both the fiducial markers found in physical space and fiducial points determined in the image space. A transformation can then be calculated to attempt to match the set of found fiducial markers in physical space and the determined fiducial points in the image space, as discussed in greater detail herein. Once an optimized or appropriate transformation has been determined, registration of the image data to the physical space can be performed in block 27.

Optionally, a fine search for fiducial points in the image data can be performed in block 26. For example, if the matching of found physical space fiducial markers and determined fiducial points in the image space does not create an appropriate number of matchable fiducial points and markers, additional fiducial points can be determined. For example, a second search based upon a position of a found fiducial marker in physical space can be used to attempt to locate an additional fiducial point in image space. It will be understood that a fine search and refinement search is not required and an appropriate number of fiducial points in image space and fiducial markers in physical space can be found initially without performing the fine search in block 26.

Figure 2:
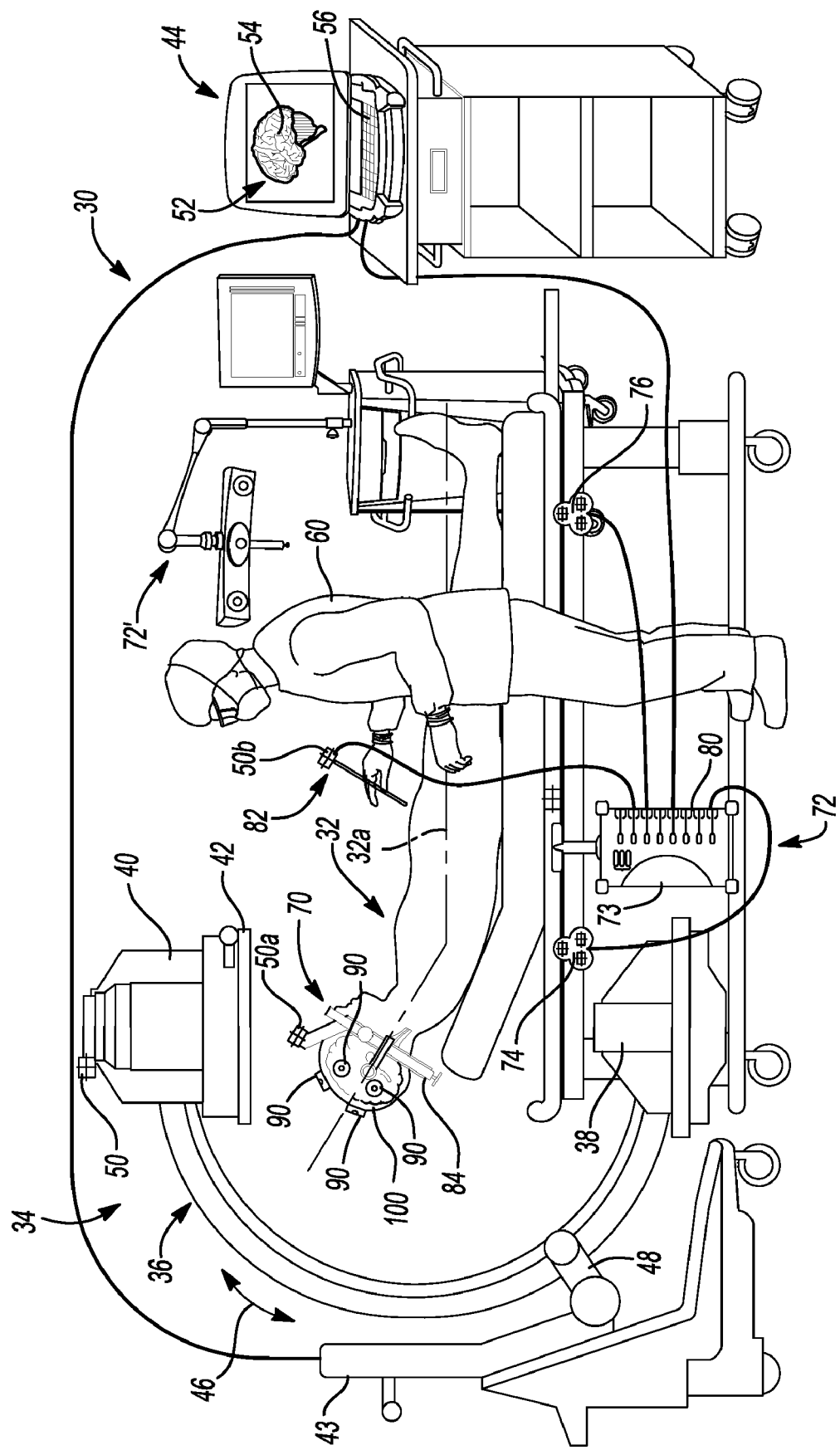
FIG. 2 is an environmental view of a surgical navigation system, according to various embodiments.

With reference to FIG. 2, a navigation system 30 that can be used for various procedures, including the system 20 is illustrated. The navigation system 30 can be used to track the location of a device 82, such as a pointer probe, relative to a patient 32 to assist in the implementation of the system 20. It should be further noted that the navigation system 30 may be used to navigate or track other devices including: catheters, probes, needles, leads, implants, etc. Moreover, the navigated device may be used in any region of the body. The navigation system 30 and the various devices may be used in any appropriate procedure, such as one that is generally minimally invasive, arthroscopic, percutaneous, stereotactic, or an open procedure. Although an exemplary navigation system 30 including an imaging system 34 are discussed herein, one skilled in the art will understand that the disclosure is merely for clarity of the present discussion and any appropriate imaging system, navigation system, patient specific data, and non-patient specific data can be used. For example, the intraoperative imaging system can include an MRI imaging system, such as the PoleStar® MRI sold by Medtronic, Inc. or an O-arm™ imaging system sold by Breakaway Imaging, LLC. having a place of business in Massachusetts, USA. It will be understood that the navigation system 30 can incorporate or be used with any appropriate preoperatively or intraoperatively acquired image data.

The navigation system 30 can include the optional imaging device 34 that is used to acquire pre-, intra-, or post-operative or real-time image data of the patient 32. The image data acquired with the imaging device 34 can be used as part of the image data in the system 20. In addition, data from atlas models can be used to produce patient images, such as those disclosed in U.S. patent application Ser. No. 10/687,539, filed Oct. 16, 2003, now U.S. Pat. App. Pub. No. 2005/0085714, entitled "METHOD AND APPARATUS FOR SURGICAL NAVIGATION OF A MULTIPLE PIECE CONSTRUCT FOR IMPLANTATION", incorporated herein by reference. The optional imaging device 34 is, for example, a fluoroscopic X-ray imaging device that may be configured as a C-arm 36 having an X-ray source 38, an X-ray receiving section 40, an optional calibration and tracking target 42 and optional radiation sensors. The calibration and tracking target 42 includes calibration markers (not illustrated). Image data may also be acquired using other imaging devices, such as those discussed above and herein.

An optional imaging device controller 43 may control the imaging device 34, such as the C-arm 36, which can capture the x-ray images received at the receiving section 40 and store the images for later use. The controller 43 may also be separate from the C-arm 36 and can be part of or incorporated into a work station 44. The controller 43 can control the rotation of the C-arm 36. For example, the C-arm 36 can move in the direction of arrow 46 or rotate about a longitudinal axis 32a of the patient 32, allowing anterior or lateral views of the patient 32 to be imaged. Each of these movements involves rotation about a mechanical axis 48 of the C-arm 36. The movements of the imaging device 34, such as the C-arm 36 can be tracked with a tracking device 50.

In the example of FIG. 2, the longitudinal axis 32a of the patient 32 is substantially in line with the mechanical axis 48 of the C-arm 36. This enables the C-arm 36 to be rotated relative to the patient 32, allowing images of the patient 32 to be taken from multiple directions or in multiple planes. An example of a fluoroscopic C-arm X-ray device that may be used as the optional imaging device 34 is the "Series 9600 Mobile Digital Imaging System," from GE Healthcare, (formerly OEC Medical Systems, Inc.) of Salt Lake City, Utah. Other exemplary fluoroscopes include bi-plane fluoroscopic systems, ceiling mounted fluoroscopic systems, cath-lab fluoroscopic systems, fixed C-arm fluoroscopic systems, isocentric C-arm fluoroscopic systems, 3D fluoroscopic systems, intraoperative O-arm™ imaging systems, etc.

The C-arm X-ray imaging system 36 can be any appropriate system, such as a digital or CCD camera, which are well understood in the art. Two dimensional fluoroscopic images that may be taken by the imaging device 34 are captured and stored in the C-arm controller 43. Multiple two-dimensional images taken by the imaging device 34 may also be captured and assembled to provide a larger view or image of a whole region of the patient 32, as opposed to being directed to only a portion of a region of the patient. For example, multiple image data or sets of data of a patient's leg, cranium, and brain may be appended together to provide a full view or complete set of image data of the leg or brain that can be later used to follow contrast agent, such as Bolus or therapy tracking. The multiple image data can include multiple 2D slices that are assembled into a 3D model or image.

The image data can then be forwarded from the C-arm controller 43 to the navigation computer and/or processor controller or work station 44 having a display device 52 to display image data 54 and a user interface 56. The work station 44 can also include or be connected to an image processor, navigation processor, and a memory to hold instruction and data. The work station 44 can include an optimization processor that assists in a navigated procedure. It will also be understood that the image data is not necessarily first retained in the controller 43, but may also be directly transmitted to the workstation 44. Moreover, processing for the navigation system and optimization can all be done with a single or multiple processors all of which may or may not be included in the workstation.

The work station 44 provides facilities for displaying the image data 54 as an image on the display device 52, saving, digitally manipulating, or printing a hard copy image of the received image data. The user interface 56, which may be a keyboard, mouse, touch pen, touch screen or other suitable device, allows a physician or user 60 to provide inputs to control the imaging device 34, via the C-arm controller 43, or adjust the display settings of the display 52. The work station 44 may also direct the C-arm controller 43 to adjust the rotational axis 46 of the C-arm 36 to obtain various two-dimensional images in different planes in order to generate representative two-dimensional and three-dimensional images.

While the optional imaging device 34 is shown in FIG. 2, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), positron emission tomography (PET), optical coherence tomography (OCT) (a more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference), intra-vascular ultrasound (IVUS), intra-operative CT, single photo emission computed tomography (SPECT), planar gamma scintigraphy (PGS). Addition imaging systems include intraoperative MRI systems such as the PoleStar® MRI system sold by Medtronic, Inc. Further systems include the O-Arm™ imaging system sold by Breakaway Imaging, LLC. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities.

Image datasets from hybrid modalities, such as positron emission tomography (PET) combined with CT, or single photon emission computer tomography (SPECT) combined with CT, could also provide functional image data superimposed onto anatomical data to be used to confidently reach target sights within the patient 32. It should further be noted that the optional imaging device 34, as shown in FIG. 2, provides a virtual bi-plane image using a single-head C-arm fluoroscope as the optional imaging device 34 by simply rotating the C-arm 36 about at least two planes, which could be orthogonal planes to generate two-dimensional images that can be converted to three-dimensional volumetric images. By acquiring images in more than one plane, an icon representing the location of an impacter, stylet, reamer driver, taps, drill, or other instrument, or probe introduced and advanced in the patient 32, may be superimposed in more than one view on display 52 allowing simulated bi-plane or even multi-plane views, including two and three-dimensional views.

Four-dimensional (4D) image information can be used with the navigation system 30 as well. For example, the user 60 can use a physiologic signal, which can include Heart Rate (EKG), Breath Rate (Breath Gating) and combine this data with image data 54 acquired during the phases of the physiologic signal to represent the anatomy at various stages of the physiologic cycle. For example, the brain pulses (and therefore moves) with each heartbeat. Images can be acquired to create a 4D map of the brain, onto which atlas data and representations of the instrument can be projected. This 4D data set can be matched and co-registered with the physiologic signal (EKG) to represent a compensated image within the system. The image data registered with the 4D information can show the brain (or anatomy of interest) moving during the cardiac or breath cycle. This movement can be displayed on the display 52 as the image data 54.

Likewise, other imaging modalities can be used to gather the 4D dataset to which pre-operative 2D and 3D data can be matched. One need not necessarily acquire multiple 2D or 3D images during the physiologic cycle of interest (breath or heart beat). Ultrasound imaging or other 4D imaging modalities can be used to create an image data that allows for a singular static pre-operative image to be matched via imagefusion techniques and/or matching algorithms that are non-linear to match the distortion of anatomy based on the movements during the physiologic cycle. The combination of a dynamic reference frame 70 and 4D registration techniques can help compensate for anatomic distortions during movements of the anatomy associated with normal physiologic processes.

With continuing reference to FIG. 2, the navigation system 10 can further include a tracking system, such as an electromagnetic tracking system 72 or an optical tracking system 72'. Either or both can be used alone or together in the navigation system 30. Moreover, discussion of the EM tracking system 72 can be understood to relate to any appropriate tracking system. The optical tracking system 72' can include the StealthStation® Treon® and the StealthStation® Tria® both sold by Medtronic Navigation, Inc. Other tracking systems include acoustic, radiation, radar, infrared, etc.

The EM tracking system 72 includes a localizer, such as a coil array 74 and/or second coil array 76, a coil array controller 73, a navigation probe interface 80, a device 82 (e.g. catheter, needle, or instruments, as discussed herein) and the dynamic reference frame 70. An instrument tracking device 50b can also be associated with, such as fixed to, the instrument 82 or instrument 82 guiding device. The dynamic reference frame 70 can include a dynamic reference frame holder 84 and a removable tracking device 50a. Alternatively, the dynamic reference frame 70 can include a tracking device 50 that can be formed integrally or separately from the dynamic reference frame holder DRF 84.

Moreover, the DRF 70 can be provided as separate pieces and can be positioned at any appropriate position on the anatomy. For example, the tracking device 50a of the DRF can be fixed to the skin of the patient 32 with an adhesive. Also, the DRF 70 can be positioned near a leg, arm, etc. of the patient 32. Thus, the DRF 70 does not need to be provided with a head frame or require any specific base or holding portion.

The tracking devices 50, 50a, 50b or any tracking device as discussed herein, can include a sensor, a transmitter, or combinations thereof. Further, the tracking devices can be wired or wireless to provide a signal emitter or receiver within the navigation system. For example, the tracking device can include an electromagnetic coil to sense a field produced by the localizing array 74, 76 or reflectors that can reflect a signal to be received by the optical tracking system 72'. Nevertheless, one will understand that the tracking device can receive a signal, transmit a signal, or combinations thereof to provide information to the navigation system 30 to determine a location of the tracking device 50, 50a, 50b. The navigation system 30 can then determine a position of the instrument or tracking device to allow for navigation relative to the patient and patient space.

The coil arrays 74, 76 may also be supplemented or replaced with a mobile localizer. The mobile localizer may be one such as that described in U.S. patent application Ser. No. 10/941,782, filed Sep. 15, 2004, now U.S. Pat. App. Pub. No. 2005/0085720, entitled "METHOD AND APPARATUS FOR SURGICAL NAVIGATION", herein incorporated by reference. As is understood the localizer array can transmit signals that are received by the tracking devices 50, 50a, 50b. The tracking device 50, 50a, 50b can then transmit or receive signals based upon the transmitted or received signals from or to the array 74, 76.

Further included in the navigation system 30 may be an isolator circuit or assembly (not illustrated separately). The isolator circuit or assembly may be included in a transmission line to interrupt a line carrying a signal or a voltage to the navigation probe interface 80. Alternatively, the isolator circuit included in the isolator box may be included in the navigation probe interface 80, the device 82, the dynamic reference frame 70, the transmission lines coupling the devices, or any other appropriate location. The isolator assembly is operable to isolate any of the instruments or patient coincidence instruments or portions that are in contact with the patient should an undesirable electrical surge or voltage take place.

It should further be noted that the entire tracking system 72, 72' or parts of the tracking system 72, 72' may be incorporated into the imaging device 34, including the work station 44. Incorporating the tracking system 72, 72' may provide an integrated imaging and tracking system. This can be particularly useful in creating a fiducial-less system. Any combination of these components may also be incorporated into the imaging system 34, which again can include a fluoroscopic C-arm imaging device or any other appropriate imaging device.

The EM tracking system 72 uses the coil arrays 74, 76 to create an electromagnetic field used for navigation. The coil arrays 74, 76 can include a plurality of coils that are each operable to generate distinct electromagnetic fields into the navigation region of the patient 32, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil array 74 is controlled or driven by the coil array controller 73. The coil array controller 73 drives each coil in the coil array 74 in a time division multiplex or a frequency division multiplex manner. In this regard, each coil may be driven separately at a distinct time or all of the coils may be driven simultaneously with each being driven by a different frequency.

Upon driving the coils in the coil array 74 with the coil array controller 73, electromagnetic fields are generated within the patient 32 in the area where the medical procedure is being performed, which is again sometimes referred to as patient space. The electromagnetic fields generated in the patient space induce currents in the tracking device 50, 50a, 50b positioned on or in the device 82, DRF 70, etc. These induced signals from the tracking devices 50, 50a, 50b are delivered to the navigation probe interface 80 and subsequently forwarded to the coil array controller 73. The navigation probe interface 80 can also include amplifiers, filters and buffers to directly interface with the tracking device 50a in the device 82. Alternatively, the tracking device 50a, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 80.

Various portions of the navigation system 30, such as the device 82, the dynamic reference frame 70, are equipped with at least one, and generally multiple, EM or other tracking devices 50a, 50b, that may also be referred to as localization sensors. The EM tracking devices 50a, 50b can include one or more coils that are operable with the EM localizer arrays 74, 76. An alternative tracking device may include an optical sensor, and may be used in addition to or in place of the electromagnetic sensor 50a, 50b. The optical sensor may work with the optional optical tracking system 72'. One skilled in the art will understand, however, that any appropriate tracking device can be used in the navigation system 30. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

In brief, the EM tracking device 50a on the device 82 can be in a handle or inserter that interconnects with an attachment and may assist in placing an implant or in driving a member. The device 82 can include a graspable or manipulable portion at a proximal end and the tracking device 50b may be fixed near the manipulable portion of the device 82 or at a distal working end, as discussed herein. The tracking device 50b can include an electromagnetic sensor to sense the electromagnetic field generated by the coil array 74, 76 that can induce a current in the electromagnetic device 50b. Alternatively, the tracking sensor 50b can be driven (i.e., like the coil array above) and the tracking array 74, 76 can receive a signal produced by the tracking device 50b.

The dynamic reference frame 70 may be fixed to the patient 32 adjacent to the region being navigated so that any movement of the patient 32 is detected as relative motion between the coil array 74, 76 and the dynamic reference frame 70. The dynamic reference frame 70 can be interconnected with the patient in any appropriate manner, including those discussed herein. Relative motion is forwarded to the coil array controller 73, which updates registration correlation and maintains accurate navigation, further discussed herein. The dynamic reference frame 70 may include any appropriate tracking sensor. Therefore, the dynamic reference frame 70 may also be optical, acoustic, etc. If the dynamic reference frame 70 is electromagnetic it can be configured as a pair of orthogonally oriented coils, each having the same center or may be configured in any other non-coaxial or co-axial coil configurations.

Briefly, the navigation system 30 operates as follows. The navigation system 30 creates a translation map between all points in the image data generated from the imaging device 34 which can include external and internal portions, and the corresponding points in the patient's anatomy in patient space. The registration occurs or is determined in block 24 of the system 20. After this map is established, whenever the tracked device 82 is used, the work station 44 in combination with the coil array controller 73 uses the translation map to identify the corresponding point on the image data or atlas model, which is displayed on display 52. This identification is known as navigation or localization. An icon representing the localized point or instruments is shown on the display 52 within several two-dimensional image planes, as well as on three and four dimensional images and models.

To enable navigation, the navigation system 30 must be able to detect both the position of the patient's anatomy and the position of the instrument 82 or attachment member (e.g. tracking device 50b) attached to the instrument 82. Knowing the location of these two items allows the navigation system 30 to compute and display the position of the instrument 82 or any portion thereof in relation to the patient 32. The tracking system 72 is employed to track the instrument 82 and the anatomy simultaneously.

The tracking system 72, if it is using an electromagnetic tracking assembly, essentially works by positioning the coil array 74, 76 adjacent to the patient 32 to generate a magnetic field, which can be low energy, and generally referred to as a navigation field. Because every point in the navigation field or patient space is associated with a unique field strength, the electromagnetic tracking system 72 can determine the position of the instrument 82 by measuring the field strength at the tracking device 50b location. The dynamic reference frame 70 is fixed to the patient 32 to identify the location of the patient in the navigation field. The electromagnetic tracking system 72 continuously recomputes or recalculates the relative position of the dynamic reference frame 70 and the instrument 82 during localization and relates this spatial information to patient registration data to enable navigation of the device 82 within and/or relative to the patient 32. Navigation can include image guidance or imageless guidance.

Patient registration is the process of determining how to correlate the position of the instrument 82 relative to the patient 32 to the position on the diagnostic or image data. To register the patient 32, the physician or user 60 may use point registration by selecting and storing particular points (e.g. fiducial points 90) from the image data and then touching the corresponding points on the patient's anatomy with the pointer probe 82. The navigation system analyzes the relationship between the two sets of points that are selected and computes a match, which correlates every point in the image data with its corresponding point on the patient's anatomy or the patient space.

The points that are selected to perform registration are the fiducial markers or landmarks 90, such as anatomical landmarks. Again, the landmarks or fiducial points are identifiable on the images and identifiable and accessible on the patient 32. The landmarks 90 can be artificial landmarks that are positioned on the patient 32. The artificial landmarks, such as the fiducial markers 90, can also form part of the dynamic reference frame 70, such as those disclosed in U.S. Pat. No. 6,381,485, entitled "Registration of Human Anatomy Integrated for Electromagnetic Localization," issued Apr. 30, 2002, herein incorporated by reference.

Figure 3:
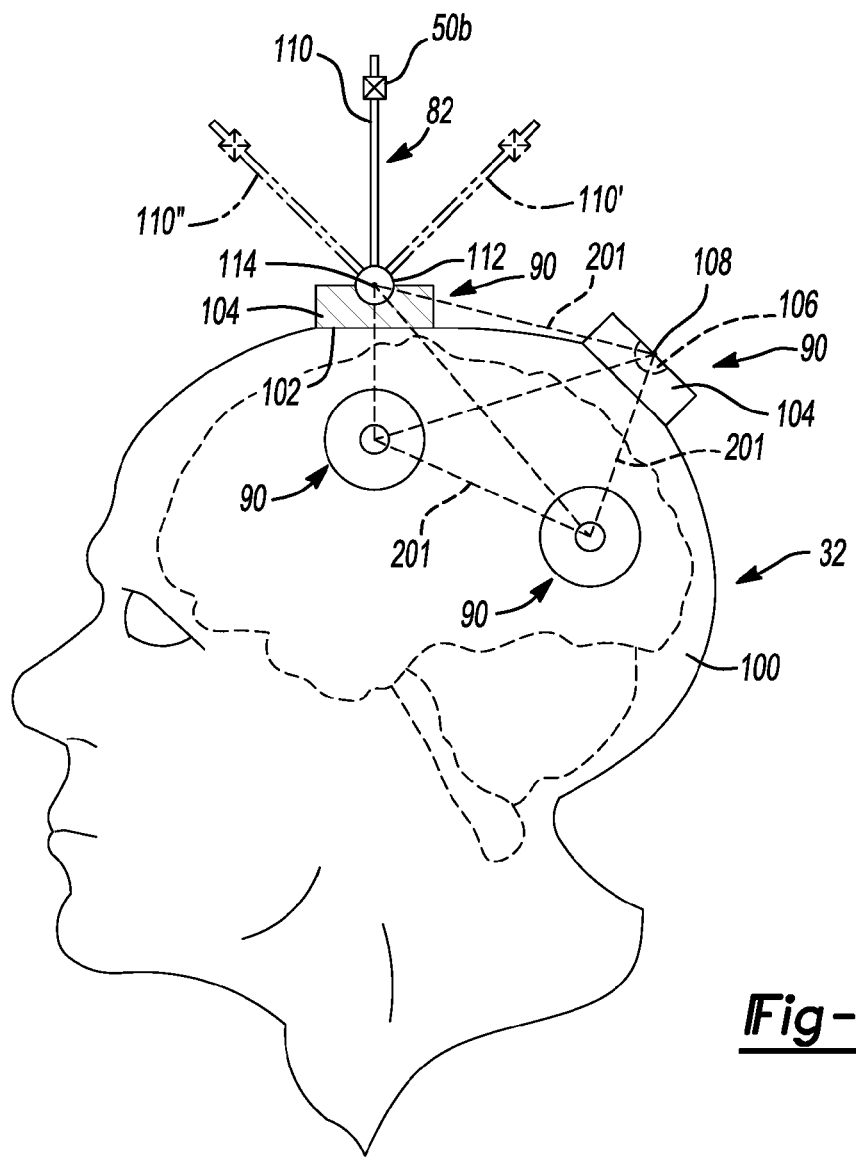
FIG. 3 is an environmental view of an anatomy with fiducial markers and pointing device, according to various embodiments, contacting the fiducial markers.

With reference to FIG. 3, the patient 32 can include one or a plurality of fiducial markers 90 affixed to the anatomy of a patient 32, such as a dermis of a cranium 100. It will be understood that any appropriate number of the fiducial markers 90 can be affixed to the patient 32 and in any appropriate location. The fiducial markers 90 can be randomly attached to the patient 32 or attached in specific locations.

The fiducial markers 90 can include any appropriate marker to be interconnected with the patient 32. For example, the makers sold by IZI Medical Products, Baltimore, Md. can be used. The markers 90 can include an adhesive base 102 that is adhered to the dermis of the cranium 100. The fiducial markers can be associated or connected to the patient 32 with an adhesive, mounting screw, clamp, etc. According to various embodiments, the fiducial markers 90 can be attached to the patient 32 prior to acquiring image data with an adhesive in a selected manner. The fiducial markers 90 can be placed in predetermined locations or in random locations for imaging.

The fiducial markers 90 can also include a body or cavity 104 extending from the base 102. The body or cavity 104 can include a material that is imageable in a selected imaging modality. For example, the cavity 104 can include a material that is imageable in a CT, MRI, a PET scan, or any appropriate scan or combination of scans. Therefore, the fiducial marker 90 can be used in one or a plurality of imaging modalities to acquire image data of the patient 32.

The fiducial marker 90 can also include a fiducial divot or identification divot 106. The divot 106 can be provided as a hemispherical or portion of the hemisphere. The divot 106 can, therefore, define a center point 108 that can be within or outside of the divot 106. The center point 108 can be used by the navigation system 30 to identify a point relative to the patient 32 for the registration of the image data to the patient space, as discussed further herein.

The center point 108 can also be referred to as a fiducial marker, in general for registration. Also, as discussed herein, the center point 108 can be the region of the fiducial marker that is identified in the image data as the fiducial point. Thus, registration can occur between the fiducial points in the image data and the fiducial markers 90 by finding the center point 108 of the fiducial markers 90.

The device 82 can include a shaft 110 to which the tracking device 50b is interconnected or associated. Extending from an end of the shaft 110 can be a device ball or contact portion 112. The device ball 112 can be substantially spherical or hemispherical to mate or contact the fiducial marker 90 divot 106 in a selected manner. The device ball 112 can also define a center point 114. The device ball 112, when associated with the divot 106, can allow the center point 114 of the device ball 112 to substantially match the center point 108 defined by the divot 106. It will be understood that a hemisphere defined by the device ball 112, rather than a complete sphere, would also allow the creation of the center point 114 that would be positioned substantially identical to a center point defined by a complete sphere.

The center point 114 will always be at a fixed location relative to the divot 106 of the fiducial marker 90 because of the interaction of the device ball 112 with the divot 106. Because the device ball 112 is at least partially spherical or hemispherical even if the shaft 110 is moved to a first position 110' or a second position 110" the center point 114 remains substantially unchanged relative to the fiducial marker 90 and the center point 108 of the fiducial marker 90. Therefore, the device 82 can contact one or a plurality of the fiducial markers 90 and the center point 114 can be determined relative to the fiducial marker 90 regardless of the orientation of device 82 relative to the fiducial marker 90.

The tracking system 72 and the navigation system 30 can then track the device 82 to determine a position of the center point 114 in physical space. The navigation system 30 or the tracking system 72 can then determine a center point 108 of the fiducial marker 90 because it substantially matches the center point 114 of the device 82. It will be understood that the center point 114, 108 are substantially artificial points in space that are defined relative to the physical devices. The center point 114, however, can also be referred to as a registration or tracked point. The tracked point can be any point on the device 82. Also, the ball 112 of the device need not be spherical, but can be a cylinder, square, etc. The navigation system 30 can determine the location of any point relative to the fiducial marker 90 for locating the fiducial marker 90. Similarly, the center point 108 of the fiducial marker 90 can be any appropriate point relative to the fiducial marker 90.

The user 60 can identify the center point of each of the fiducials interconnected or associated with the patient 32 by moving the device 82 to associate it with each one. This can allow the identification of the center point 108 and each of the fiducial markers 90 to be used by the navigation system 30 to identify the position of the fiducial markers 90 in the physical space. In addition, as discussed further herein, the navigation system 30 or any appropriate system can then determine a correlation or registration of the image data, which can include a determined fiducial point related to the center point 108 of the fiducial marker 90, and the tracked center point 108 of the fiducial marker 90 based upon the tracking of the device 82.

The navigation system 30 may also perform registration using anatomic surface information or path information as is known in the art (and may be referred to as auto-registration).

The system 10 may also perform 2D to 3D registration by utilizing the acquired 2D images to register 3D volume images by use of contour algorithms, point algorithms or density comparison algorithms, as is known in the art. An exemplary 2D to 3D registration procedure is set forth in U.S. Ser. No. 10/644,680, now U.S. Pat. App. Pub. No. 2004/0215071, entitled "Method and Apparatus for Performing 2D to 3D Registration" filed on Aug. 20, 2003, hereby incorporated by reference.

Also as discussed herein, a substantially fiducial-less registration system can be provided, particularly if the imaging device 34 and the tracking system 72 are substantially integrated. Therefore, the tracking system 72 would generally know the position of the imaging device 34 relative to the patient 32 and fiducials may not be required to create registration. Nevertheless, it will be understood that any appropriate type of registration system can be provided for the navigation system 30.

In order to maintain registration accuracy, the navigation system continuously tracks the position of the patient 32 during registration and navigation. This is because the patient 32, dynamic reference frame 70, and transmitter coil array 74, 76 may all move during the procedure, even when this movement is not desired. Alternatively the patient 32 may be held immobile once the registration has occurred, such as with a head frame. Therefore, if the navigation system 30 did not track the position of the patient 32 or area of the anatomy, any patient movement after image data acquisition would result in inaccurate navigation within that image. The dynamic reference frame 70 allows the electromagnetic tracking system 72 to register and track the anatomy. Because the dynamic reference frame 70 is rigidly fixed to the patient 32, any movement of the anatomy or the coil array 74,76 is detected as the relative motion between the coil array 74,76 and the dynamic reference frame 70. This relative motion is communicated to the coil array controller 73, via the navigation probe interface 80, which updates the registration correlation to thereby maintain accurate navigation.

The navigation system 30 can be used according to any appropriate method or system. For example, image data, atlas or 3D models may be registered relative to the patient and patient space, as discussed further herein. Generally, the navigation system 30 allows the images on the display 52 to be registered and accurately display the real time location of the various instruments and other appropriate items, such as the trackable pointer. In addition, the pointer may be used to register the patient space to the pre-acquired image data or the atlas or 3D models. In addition, the dynamic reference frame 70 may be used to ensure that any planned or unplanned movement of the patient or the array 74, 76 is determined and used to correct the image on the display 52.

To obtain a maximum reference, it can be selected to fix the dynamic reference frame 70 in each of at least 6 degrees of freedom. Thus, the dynamic reference frame 70 can be fixed relative to axial motion X, translational motion Y, rotational motion Z, yaw, pitch, and roll relative to the portion of the patient 32 to which it is attached. Any appropriate coordinate system can be used to describe the various degrees of freedom. Fixing the dynamic reference frame relative to the patient 32 in this manner can assist in maintaining maximum accuracy of the navigation system 30.

The instrument 82 can be a deep brain stimulation (DBS) lead, a micro-electrode (ME) for a recording device, a catheter, etc. and each can include at least one of the tracking devices, such as the tracking device 50b. The tracking device 50b can be any appropriate tracking device and can be formed in any appropriate manner such as the catheters described in pending U.S. patent application Ser. No. 11/241,837, filed on Sep. 30, 2005, now. U.S. Pat. App. Pub. No. 2006/0084867, entitled "METHOD AND APPARATUS FOR SURGICAL NAVIGATION," incorporated herein by reference.

The device 82 can also be a therapy delivery device, which can deliver a material to a selected portion of the patient 32. The material can be any appropriate material such as a bioactive material, a pharmacological material, a contrast agent. Instead of a material, a therapy such as electrical stimulation can be used with a DBS. The DBS can be used to apply a voltage, a pulse width, etc. to a selected portion of the brain.

As mentioned briefly above, the display 52 can display any appropriate type of image data 54. For example, the image data 54 can include patient specific image data that can be acquired at any appropriate time. The image data can include magnetic resonance imaging data (MRI) that can provide structural anatomical image data of the patient 32. The image data 54 can be displayed on the display 52 for use during a procedure by the user 60. The display on the display 52 can also include various atlas image data. Atlas image data can include two-dimensional image data sets, three-dimensional image data sets, and even four-dimensional image data sets that show the change of various anatomical structures over time.

Figure 6:
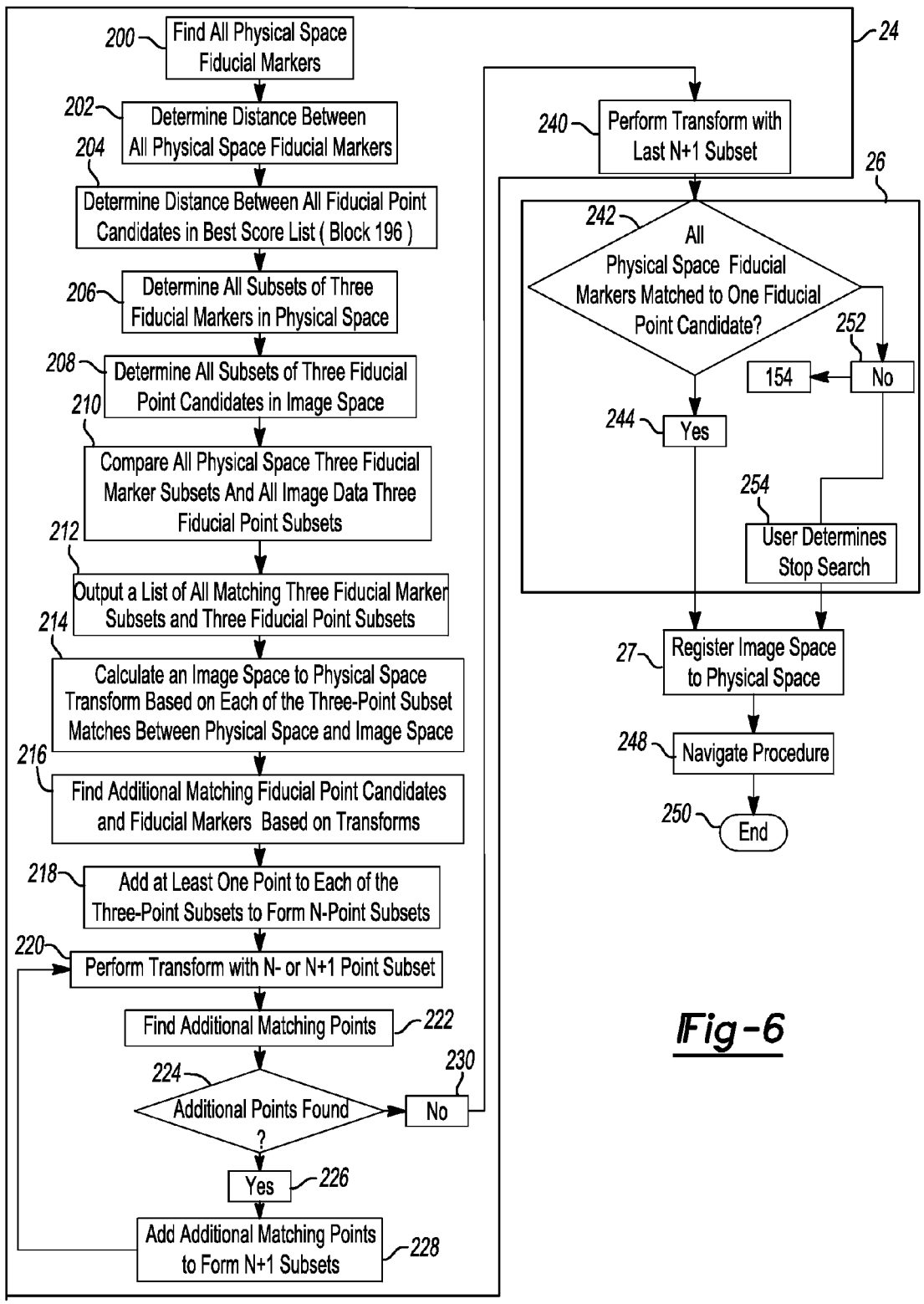
FIG. 6 is a detailed flow diagram of a portion of the process illustrated in FIG. 1.

Once the navigation system 30 has registered the image data to the patient space, navigation of an operative instrument or other tracked instrument can occur. As discussed above, the tracked instrument can be any appropriate instrument and can include the pointer probe 82 used in a registration or fiducial marker finding process. Also, as discussed above, various methods and techniques can be used to register the image space to the patient space. Although multiple techniques can be used, an exemplary system is illustrated in FIGS. 1, 4 and 6. The exemplary system can be used to register the patient space and the image space so that a procedure can be navigated with the navigation system 30.

With reference to FIG. 4 and returning reference to FIG. 1, the identification of fiducial points in block 22 is illustrated in greater detail in FIG. 4. Identification of fiducial points, as illustrated in block 22 and FIG. 4, includes identifying at least one fiducial point in the image data. The fiducial markers 90, as discussed above, can be associated with the patient 32 in any appropriate manner. For example the user 60 can randomly place the fiducial markers 90 on the patient 32 prior to imaging near an area that will be within the navigation field. The fiducial markers 90 can then be imaged with the patient 32.

The fiducial point in the image data can include the point that define the fiducial marker 90 that was associated with and imaged with the patient 32. The fiducial marker 90, therefore, includes a physical space presence and an image data space presence as a fiducial point. Therefore, the identification of the fiducial points in block 22 is an identification of the fiducial points or data in the image data that define or were created by the fiducial marker 90.

It will be understood, that the fiducial points can be any appropriate type of data from the image data including pixels, voxels, and the like. Further, identification of fiducial points in the image data can include the identification of the center point 108 of fiducial marker 90 in the image data. Accordingly, the identification of the fiducial points can include identification of each of the pixels or voxels that identify a fiducial marker in image data. Further the center point or fiducial points can be a single point, such as a pixel or voxel, defined by the fiducial points.

The image data acquired of the patient 32 and the fiducial markers 90 can be any appropriate type of image data, as discussed above. For example, the image data can include MRI image data, computed tomography image data, and ultrasound image data acquired of the patient. Moreover, the image data can be 2D, 3D, or 4D image data.

According to various embodiments, image data of the cranium of the patient can be obtained. It will be understood that the exemplary process can be applied to any appropriate image data. First the image can be segmented in block 148. Image segmentation can occur according to any appropriate processable algorithm, such as using a grey value threshold, region growing, or any appropriate segmentation method. The segmentation process in block 148 can, according to various embodiments, identify the object which is imaged from the background. Once the object is identified and segmented from the background a surface distance transformation can be calculated in block 150.

The distance transformation identifies the distance of every point in the image data from the closest point on the edge of the segmented object. Each of the pixels or voxels can then be given a value based on the distance from the edge. The value can be equal to the pixel or voxel distance from the edge or any appropriate distance value. The distance transformation, however, identifies the distance of every point in the image data from the edge of the segmented object to assist in the determining or for the determination of an edge or surface of the object in the image data.

The distance transformation calculation in block 150 can allow for the identification or extraction of surface points in block 152. The surface points identified in block 152 can substantially define the surface or the outer most portion of the imaged region. For example, the surface points can include the surface of the skin, the surface of the fiducial markers 90, or the like of the imaged patient.

The extraction of the surface points in block 152 can be performed according to any appropriate method. For example, once the distance transformation is calculated in block 150, the points that are at a selected distance can be identified as the surface points. For example, the image data points that are determined to have a value of "zero" can be identified as the surface of the imaged portion or object. The value of zero can be based upon the distance from the segmented background.

Further, the extraction of surface points allows a minimization of the points in the image data to be searched for identifying the fiducial markers points. The surface points will be understood to include all of the possible image data portions that can include image data relating to the fiducial points. As discussed above, the fiducial markers 90 can be adhered to an exterior or surface of the patient 32. It will be understood, however, that the surface points may not include all of the possible points of the fiducial markers if the fiducial markers are embedded or below the surface of the patient. Therefore, the extraction of surface points for the fiducial point determination is not necessary and may not be used according to various embodiments.

Once the surface points of the image data have been extracted, various calculations and refinement can be made to the image data. First, a tangential resection data set can be formed in block 154. The tangential data set formed in block 154 can include a data set defined by plurality of tangent planes to each of the points that are defined on or at the surface in block 152.

Figure 5:
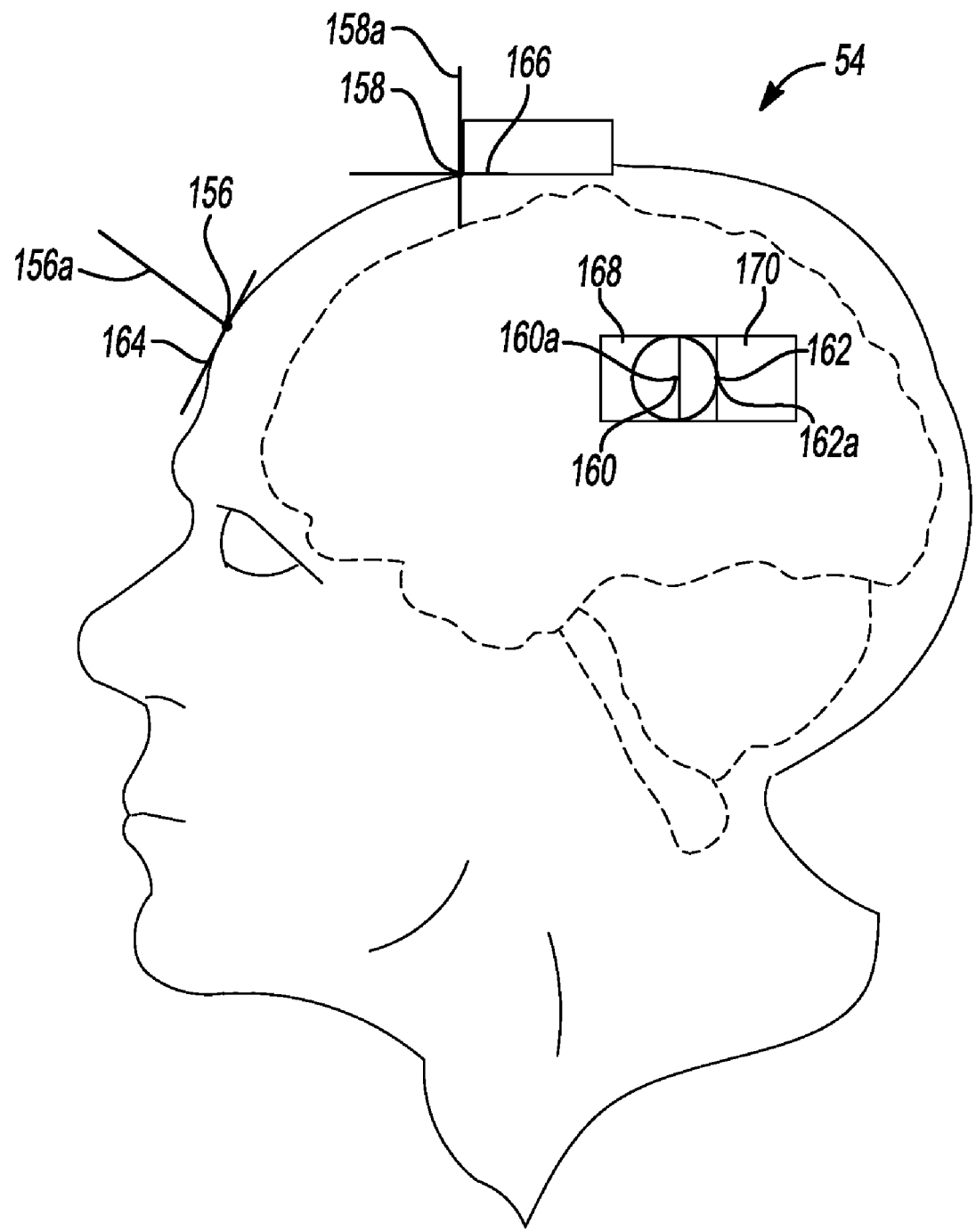
FIG. 5 is exemplary image data.

With reference to FIG. 5, the image data 54 can include the extracted surface points. The extracted surface points can include, a first point 156, a second point 158, a third point 160, and a fourth point 162. The exemplary points 156-162 can be understood to simply be exemplary of a plurality of points extracted to define an entire surface in the image data. Nevertheless, for clarity of the current discussion, only four points are used. A line 156a-162a normal to the surface at each point can then be determined. A tangent plane or area can be determined or defined perpendicular to each of the lines 156a-162a. For example, a first tangent plane 164 can be defined near the first point 156. A second tangent plane 166 can be defined near the second point 158. A third tangent plane 168 can be defined near the third surface point 160. A fourth tangent plane 170 can also be defined near the fourth surface point 162.

Each of the tangent planes 164-170 can be formed substantially perpendicular to the lines 156a-162a. The tangent planes 164-170 can also be formed of any appropriate size. The tangent planes 164-170 can be sized to resect a portion of the image data near a selected point, rather than the entire data set. Therefore, the tangent planes 164-170 are generally referred to as local tangent planes. It will be understood, however, that the tangent planes can have any appropriate size or dimension.

The tangent planes identify or define selected two-dimensional areas of the image data 54. As discussed above, the image data 54 can include or be defined as a three-dimensional model of the object, including the patient 32. The tangent planes 164-170 can identify selected two-dimensional data from the image data 54 obtained of the patient 32. The resection of the three-dimensional data to two-dimensional data by the tangent planes 164-170 can allow for an initial application of a two-dimensional template, as discussed further herein, to the image data.

The points 156-162 are exemplary points for clarity of this discussion, but one skilled in the art will understand that a tangent plane can be created for each point in the image data 54 or any appropriate number of points in the image data. For example, for speed of the calculation, half of the points defined in the image data, a quarter, or any appropriate portion of the points can be used as points to perform a tangential or 2D resection. In other words, a subset of the points in the image data can be selected for the tangential resection rather than creating a tangent plane for all of the points in the image data. Thus, any appropriate number of tangent planes can be formed in any appropriate number relative to the image data 54 for purposes discussed further herein. Moreover, the image data or pixels defined by each of the tangent planes 164-170 can be immediately compared to a template, as discussed further herein, or stored sequentially or in any other appropriate manner for later analysis.

A fiducial template can then be formed or determined in block 180. The fiducial template formed in block 180 can be formed at any appropriate time. For example, the fiducial template in block 180 can be stored in a memory system of the workstation 44 to be used within the navigation system 30. The fiducial template formed in block 180 generally defines a surface of the fiducial marker 90. The template formed in block 180 can be a physical template defined by the metes and bounds of the fiducial marker 90 or defined substantially as how the fiducial marker 90 would be imaged by the selected imaging modality.

Thus, the fiducial template formed in block 180 can be a computer readable definition of the fiducial marker 90 that would appear in the image data. The fiducial template defined or formed in block 180 can be defined graphically for use within the workstation 44 or any appropriate processor system. The fiducial template can then be matched to the tangential resection data set in block 182. Moreover, the fiducial template formed in block 180 can include a definition of the fiducial point that can relate to the center point 108 of the fiducial marker 90.

The fiducial template can be matched to the tangential resection data in block 182, according to any appropriate method. The workstation 44, or any appropriate processor system, can be used to match the fiducial template definition to the surfaces defined in the tangential resection data set formed in block 154. It will be understood that the tangential data set can substantially define 2D data from the image data 54.

The tangential data set formed in block 154 can be stored or categorized in any appropriate manner. The fiducial template formed in block 180 can be applied or compared to the organized data set to determine whether any portion of the data from the tangential resection data formed in block 154 matches or substantially matches the formed fiducial template in block 180. The matching or comparison occurs in block 182 and an initial list of 2D fiducial point candidates can be output in block 184. The initial fiducial point candidate list can be output in block 184 in any appropriate manner. For example, a human readable output can be produced or a system memory output can be produced.

The initial fiducial point candidate list of 2D candidates output in block 184 can be ordered or scored based upon a percentage match, comparison match, or any appropriate comparison procedure. The score output as a part of the initial fiducial point candidate list in block 184 can include any appropriate scoring system and can include either all of the data blocks including any possible fiducial point candidate or only those above a threshold matching score. The initial list can be sorted in block 186. Again, the sorting in block 186 can be used to identify each of those data blocks that reach a threshold or can be used for efficiency in a matching system, such as further matching or refining only a selected number or score of the initial fiducial point candidate list.

Once the list of 2D fiducial point candidates are sorted in block 186, a 3D fiducial template can be formed in block 188. Again, it will be understood, that the 3d fiducial template formed in block 188 need not be formed during an operative procedure, such as when a registration is occurring, but can be formed at any appropriate time. Further, the 3D fiducial template can be stored in the memory system of the workstation 44 for use by the navigation system 30 during the registration procedure.

The 3D fiducial template can be substantially similar to the 2D fiducial template, save that it is in a three dimensional form. When the fiducial marker 90 is similar to that illustrated in FIG. 3, the 3D fiducial template can be substantially defined as an outer cylinder and an inner cylinder. In other words, the fiducial template can define a toroid or similar shape. The two cylinders can define the 3D fiducial template for comparing to the 3D image data. Again, the 3D fiducial template can include a computer readable graphical definition of the fiducial marker for comparison to the image data to determine or identify fiducial points or fiducial point candidates.

The fiducial template, either the 3D or the 2D fiducial template, can define any appropriate geometric shape. For example, the fiducial template can define any geometric shape which is defined by the fiducial marker 90. Therefore, the fiducial templates and the fiducial marker can be toroidal, square, polygonal, irregularly shaped, regularly shaped, or any appropriate shape. Therefore, the exemplary toroidal or cylinder within a cylinder shape is merely exemplary.

Moreover, the fiducial template can be defined by an intensity gradient. For example, the three-dimensional fiducial template can be defined as or described as a volumetric intensity template. The volumetric intensity can be defined or described in a computer readable format for comparison to the image data. The intensity configuration can be compared to the image data to identify a position or that part of the image data that can include a fiducial marker. Therefore, the templates, as discussed herein, can be defined by geometric shapes, intensity definitions, volumetric shapes, or any appropriate definition. The toroidal shapes are merely exemplary and used for the clarity of the current discussion.

The template can include a definition or an identification of the point that will be identified as the fiducial point. As discussed above, the fiducial points need not be within the center or at a defined geometrical location within the fiducial marker that is imaged. The point imaged in the image data or tracked with the device 82 can be defined at any appropriate location relative to the device 82 positioned relative to the fiducial marker 90.

The 3D fiducial template can be compared to the image data in block 190. The 3D fiducial template can be compared only to the portion of the image data that is defined by one of the candidates from the sorted list in block 186. This can be performed for various purposes, such as efficiency of the determination of the fiducial points, speed of the process, etc.

The 3D fiducial template can be compared to the image data acquired of the patient 32 and of the fiducial marker 90. Although the tangential resection data set in block 154 can be used for the 2D match, the 3D match or comparison can occur using the unresected three dimensional image data acquired directly from the imaging system. Thus, both a 2D and a 3D comparison can occur.

Although the image data acquired from the imaging system can be substantial in size, the list of the fiducial point candidates from block 186 can substantially minimize or limit the amount of comparison or processing time required. Again, the image data can be organized in any appropriate manner, such as including a plurality of data blocks. Further, the image data can be pixel image data, voxel image data, or any appropriate portion of the image data for comparison to the 3D fiducial template in block 190.

Further, the comparison of the 3D fiducial templates to the image data in block 190 can be performed in any appropriate manner. The image data can be prepared as a list of data points for comparison to the 3D fiducial template in a systematic comparison method with a graphical comparison. It will be understood that any appropriate comparison method can be used to determine a match between the 3D fiducial template and the image data.

After the comparison of the 3D fiducial template to each from the initial fiducial point candidate list in block 186, a score can be made and a second list of fiducial point candidates is output in block 191. Again the output can be an internal output or a human readable output. The score can be computed based upon a percentage match, a system match, or the like between the 3D fiducial template and the image data.

The initial list of candidates from block 186 can then be re-ordered and sorted based upon the 3D score in block 192. The second list of candidates in block 192 can be each of the fiducial point candidates from the two dimensional candidate list in block 186 or can include a shortened list based upon a threshold score or other criterion. The second list of candidates can be provided or reduced to a selected number, for efficiency and speed of the later registration. Regardless, the second list of fiducial point candidates in block 192 can include a best or optimized list of the candidates that match the 3D fiducial template.

Once the list is sorted based upon the 3D score, which can include about 40 candidate fiducial points, a determination of a correct orientation and position of the highest scoring fiducial point candidates can be made in block 194. Determining the correct orientation and position of high scoring fiducial point candidates can include determining a possible position of the candidate fiducial point relative to the remaining portion of the image data.

Further, the correct position and orientation determination of the fiducial point candidates can also be more clearly or completely determined by comparison to the 3D fiducial template. The correct orientation and position determination can be performed on the points that may define the fiducial point candidate, with less tolerance, with tighter criterion, etc. Moreover, the determination of the position and orientation of the fiducial point candidate can also require additional data analysis to properly match the 3D fiducial template to the fiducial point candidate in the image data.

The 3D fiducial template can be point by point compared to the fiducial point candidates to determine a more exact or probabilistic match. The comparison can also determine whether the 3D fiducial template, which has a predetermined "top," "bottom," "side," "internal cylinder," (as illustrated in FIG. 3) can be determined. The fiducial point candidates can be compared to the 3D fiducial template to substantially determine and match the various portions of the 3D fiducial templates to the fiducial point candidates. In this way, an appropriate position and orientation of the fiducial point candidates can be determined.

The comparison can also have lower tolerances and allow for the provision of a score of each of the sorted list of candidates in block 192. The scoring can again be based upon a comparison match, or other appropriate scoring techniques to determine a match or score of a match between the fiducial template and the fiducial point candidates. The scored list can then be sorted in block 196 to produce a final candidate list of fiducial points.

The final sorted list in block 196 can include any appropriate number, such as about 20 final fiducial point candidates. The final list can be pared down from the initial fiducial point candidates list in block 184 that can include any appropriate number, such as about 400 fiducial point candidates. The fiducial point and identification process in block 22, however, can use the various reducing techniques, such as an initial 2D comparison, a first 3D comparison, and a final 3D comparison to efficiently and quickly determine a best or optimized list of fiducial point candidates.

It will be understood by one skilled in the art that the initial comparison of 2D data can be based upon or use less intensive calculations or processing steps. Each successive comparison can use a computationally more intensive process on fewer and fewer candidate points. Therefore, the final list produced in block 196 can be based upon a final comparison of approximately 40, or any appropriate number of fiducial point candidates to make the final list. Moreover, the processing to determine the fiducial point candidates can occur in any appropriate processor or at any appropriate time. For example, the workstation 44 can include a processor to determine the list of fiducial point candidates. In addition, a different processor can determine the list of the fiducial point candidates at any time after the image data is acquired, such as pre- or intra-operatively.

In addition, the fiducial templates can include computer readable templates. The computer readable templates can be compared to the image data based upon an algorithm, as discussed above. Moreover, the comparison can be understood to be a virtual and systematic comparison of the fiducial template to the image data. According to various embodiments, the fiducial template can be overlaid on the image data to determine fiducial point candidates in the image data.

With reference to FIG. 6, the matching and transformation process of block 24, the fine search procedure of block 26, and registration in block 27 are illustrated in further detail. The matching and registration process uses the fiducial point candidates determined in block 22, illustrated in FIGS. 1 and 4, and registers or correlates them to points and physical space. As discussed above, the fiducial markers 90 can identify one or more points that can be correlated or registered to points in image space.

Beginning in block 200, all of the fiducial markers in physical space can be found. With reference to FIG. 3, the fiducial markers 90 can be positioned relative to the patient 32 in any appropriate manner, such as with an adhesive. It will be understood, by one skilled in the art, that any appropriate fiducial markers can be used for the system 20. Nevertheless, fiducial markers 90 allow the pointer device 82 to interact with the fiducial markers 90.

As discussed above, the device 82 can be tracked with the tracking device 50b by the tracking system 72. Therefore, the navigation system 30 can determine the center point 114 in physical space. The center point 114 can define the fiducial marker in physical space. Therefore, the user 60 can move the pointer device 82 to interact with each of the plurality of the fiducial markers 90 associated with the patient 32. The position of the fiducial markers 90 can be stored in the memory system of the workstation 44 or any appropriate system.

According to the various embodiments, the fiducial markers 90 can be found by the user 60 in any order. The user 60 can move the device 82 and contact or associate the device 82 with the fiducial markers in any order or appropriate manner. Moreover, the user 60 need not manually associate the found fiducial markers 90 with the fiducial point candidates from block 196. As discussed further herein, the process 24 determines matches between at least a number of the fiducial point candidates from block 196 and the found fiducial markers 90.

Once all of the fiducial markers are found in physical space in block 200 a determination of the distance between each of the fiducial markers in physical space can be made in block 202. With reference to FIG. 3, each of the fiducial markers 90 exists at a distance from each of the other fiducial markers 90. The distance between each of the plurality of fiducial markers can be identified by a distance line 201 which can include a plurality of distance lines 201. It will be understood that the number of distance lines 201 can depend upon the number of the fiducial markers 90 associated with the patient 32. Again, the distances between each of the fiducial markers can be stored in the memory system associated with the workstation 44.

The distances between fiducial markers in physical space can be determined by the navigation system 30. Because the navigation system 30 includes the physical location of the fiducial markers in the physical space, the distance between the fiducial markers in physical space can be determined relative to a coordinate system of the physical space. The distance between the fiducial markers can be determined in any appropriate unit, such as metric units, English units, or any appropriate units.

A determination of a distance between all of the fiducial point candidates in the final list from block 196 can also be determined in block 204. The final list fiducial point candidates from block 196 can include any appropriate number of fiducial point candidates. Nevertheless, a distance between each of the fiducial point candidates to each of the other fiducial point candidates can be determined in the image data. A processor, such as the processor associated with the workstation 44, can determine the plurality of distances between each of the fiducial point candidates and all of the other fiducial point candidates. The determination of a distance between each of the fiducial markers 90 and all of the other fiducial markers 90 and each of the fiducial point candidates and all of the other fiducial point candidates can define a plurality of special configurations defined by two or more of the fiducial markers 90 or the fiducial point candidates.

In block 206, the special orientation or position of the plurality of the fiducial markers in physical space can be divided into a plurality of subsets of just three of the fiducial markers in block 206. The navigation system 30 or any appropriate portion thereof or any other processor, can determine a plurality of three-fiducial marker subsets including only three of the fiducial markers found in the physical space in block 200. Each of the three-fiducial marker subsets will be defined by three fiducial markers and the distances between each of them. It will be understood, that the number of subsets can depend upon the number of fiducial markers associated with the patient 32. For example, if four fiducial markers were associated with the patient 32, there would be three possible subsets including distances between the four fiducial markers. In other words, three groups identifying three different groups of the four exemplary fiducial markers can be formed (if order is not a determined or relevant). The three-fiducial marker subsets, which include all of the subsets of three of the fiducial markers, can be stored in a memory system. The three-fiducial marker subsets can be stored for appropriate procedures as discussed herein.

A determination of all subsets of three fiducial points in the image space can also be determined in block 208. Similar to the three-fiducial marker subsets in physical space determined in block 206 a determination of all three-fiducial point subsets in image space can be determined based upon the distance between the fiducial points in block 204. Again, the plurality of three-fiducial point subsets will be dependent upon the number of the candidate fiducial markers in the final list from block 196.

A comparison of all of the three-fiducial marker subsets and the three-fiducial point subsets can be done in block 210. The comparison can compare the distances between each of the three-fiducial marker subsets and the three-fiducial point subsets that are determined in blocks 206 and 208. A match between one of the three-fiducial marker subsets and the three-fiducial point subsets can be based upon a predetermined or selected tolerance. For example, if a first three-fiducial marker subset matches a first three-fiducial point subset within a selected tolerance, such as plus or minus one millimeter, a match can be determined. The tolerance, however, can be any appropriate amount to allow for more or fewer of possible matches. The tolerance can also include an orientation discrepancy, angle, etc.

A list of matches or possible matches between the subsets of the fiducial markers and the subsets of the fiducial points can be output in block 212. The output in block 212 can be any appropriate output such as a human readable output or a computer memory output. The output list can also include a score of the matches determined based upon the comparison in block 210. The scores can be based upon the amount of tolerance needed to create the match, the configuration of the match, or any other appropriate scoring technique. Regardless, the output list in block 212 can include a list of all of the three-fiducial marker subsets that are determined to match at least one of the three-fiducial point subsets.

Once the list of all matches is output in block 212, a transformation between the image space and physical space can be calculated for each of the matches in block 214. The transformation between the image space and the physical space can be calculated according to any appropriate method, such as those generally understood in the art. The transformation calculated between the image space and the physical space can create a "preliminary registration". The transformation attempts to transform or correlate each of the points in the image space with each of the points in the physical space. The transformation, based upon the three point subsets may, however, be sub-optimal. Nevertheless, the transformation calculated based on the three point subset matches can correlate points beyond the points identified in the three point subsets.

For example, additional matching points between the image space and the physical space can be found in block 216. A first transformation based upon a match of one of the three point subsets can identify the correlation of other points between the image space and the physical space. When the transformation identifies further correlating or matching points the additional points can be added to the respective subset. Again, it will be understood, that the matching of correlation can be that defined within a certain parameter. For example, a correlation or match can be determined if the points are within a preset threshold, such as about one millimeter to about three millimeters.

The determination or finding of additional points that correlate can allow for the addition of the points to a respective three point subset. For example, in an iterative process, one point may be added to a respective subset to define a four-fiducial point subset and a four-fiducial marker subset in block 218. It will be further understood that points can be added to the subsets in any appropriate number such as 1, 2, or more. Further, it will be understood that the additional points can be added to the subsets for both the image data and the physical space. Further, the points can be added to the transformation or to refine the transformation set rather than to the individual subsets alone.

The additional points, however, can be added to the subsets to create a new list of N-fiducial point subsets or N-fiducial marker subsets. N can be any appropriate number, such as four. The N-fiducial point subsets or N-fiducial marker subsets are exemplary subsets that can include a N number fiducial points or a N number of fiducial markers. As discussed above, a first subset can include three fiducial points or three fiducial markers. Therefore, N can be 3. As further discussed above, a first transformation can identify additional matching fiducial markers to fiducial points. The addition of one fiducial marker or one fiducial point to a particular subset can create an N+1 subset of fiducial markers or fiducial points. Therefore, as discussed herein, the N or N+1 fiducial marker or fiducial point subsets refers to the number fiducial markers or fiducial points in the particular subset that can be or has been matched to a corresponding subset. Accordingly, the exemplary inclusion of three fiducial markers or three fiducial points in a particular subset is merely for purposes of the above discussion and can be used as an initial subset or creation of subsets for matching to the corresponding fiducial marker or fiducial point subsets.

The new list of subsets based upon the N-fiducial point subsets or N-fiducial marker subsets in block 218 can be the same number or greater or less than the number of subsets output in block 212. As one skilled in the art will understand, the additional points added to the three-fiducial point or three-fiducial marker subsets can create additional possible subsets for matching between the image space and the physical space.

Once the N-fiducial point subsets or N-fiducial marker subsets are created, a new transformation can be performed in block 220 based upon matched N-fiducial point subsets or N-fiducial marker subsets. The N-fiducial point subsets or N-fiducial marker subsets, which can include any appropriate number of points, can create a transformation or correlation between the image space and the physical space. The transformation or the calculation thereof can be substantially similar to that in block 214. The differences being that additional points can be used in performing the transformation.

Once the transformation is performed in block 220, additional points can be found in block 222. The finding of the additional points can be similar to the finding of additional points in block 216, but based on the new transformation. Again, the additional points can be found based upon a tolerance of matching of points between the image space and the physical space. The tolerance can be similar or different to that used in block 216. For example, a lower tolerance may be used in finding the additional points in block 222 to further narrow the possible matches. After all possible additional matching points are found, a determination step of whether additional points are found is determined in decision block 224. If further matching points are found in block 222, then the determination of YES 226 can allow for the addition of points to form a N+1-fiducial point subsets or N+1-fiducial marker subsets in block 228. If the N+1-fiducial point subsets or N+1-fiducial marker subsets is formed in block 228 a transformation can be performed using the N+1-fiducial point subsets or N+1-fiducial marker subsets in block 220 and the process is repeated to create appropriate N+2, N+3, etc. Therefore, the iterative process can continue to add additional points to a selected subset if matches can be made. Again, the creation of the N-fiducial point subsets or N-fiducial marker subsets can include any appropriate initial number of fiducial points or fiducial markers. The N+1, N+2, etc. subsets are understood to include an additional +1, +2, etc. matched fiducial point or marker in that subset. Also, N+2, etc. is relative to the first N group, thus each iteration can include one additional point or marker, i.e. N+1, compared to the immediately preceding subset. Each time points are added a similar or different tolerance can be used to assist in the process.

If no additional points are found in decision block 224, then the NO block 230 can be followed to perform a transform with the last N+1-fiducial point or N+1-fiducial marker subsets in block 240. The determination that no additional points are found can mean that no further points are within a tolerance set by the system 24. As discussed above, the points being matched can include the determined fiducial points in the image data and the found physical space fiducial markers in block 200. Therefore, if no further points are found to match after the final transformation then a transformation with the N+1-fiducial point or N+1-fiducial marker subsets can be used to correlate each of the points in the physical space to the image space.

Once the transformation with the N+1-fiducial point or N+1-fiducial marker subsets is performed in block 240, a determination of whether all the fiducial markers in physical space have been matched to fiducial points in image space can be done in decision block 242, which can be the beginning of the fine search procedure in block 26. The determination can determine whether all of the physical space fiducial markers found in block 200 have been matched to a fiducial point candidate in the image space. For example, the patient 32 can have six fiducial markers attached during imaging and all of the six can be found in block 200. The N+1-fiducial point or N+1-fiducial marker subsets transformation in block 240 can perform a transform based upon the matching of six fiducial points in the image data to six fiducial markers found in block 200. Therefore, the YES determination in block 244 would be found and a final transformation and registration of the image space to the physical space can be performed in block 27. The transformation in block 27 can be a registration of the image space to the physical space based upon the transformation equation or calculation determined based upon the transformation of the fiducial markers to the fiducial points. The registration can register or correlate every point in the image data to a point in the physical space coordinate system based upon the transformation of the fiducial point to the fiducial markers. Once the registration occurs, a navigated procedure can occur in block 248, which can include an imaged navigation procedure and the procedure can then end in block 250. Ending the procedure can include various steps, however, such as closing an incision, providing a therapy, implanting an implant, or the like.

Physical space fiducial markers found in 200 can include six fiducial markers, as discussed above. The N+1-fiducial point or N+1-fiducial marker subsets transformation in block 240, however, can be based upon only five fiducial points being found in the iterative process, therefore, the determination in decision block 242 can be NO 252. If NO in block 252 is determined, where all of the fiducial markers have not been found in the image space, a user can determine to stop the matching in block 254 and proceed to the registration in block 27. For example, the system can perform a registration with any appropriate number of fiducial markers, such as less than the number positioned and imaged with the patient 32. Therefore, the user 60 can determine to perform the registration with an appropriate number of the matched fiducial markers to the fiducial points. A matched number can be less than a number of fiducial markers, but enough to provide an appropriate registration, such as within a selected error threshold.

If the user does not determine to stop the matching in block 254, however, the process can return in the system 20 beginning with block 154 of the process 22, illustrated in FIG. 4, to begin, in earnest, the fine or refinement search for fiducial points to match to the missed or unmatched fiducial marker 90. The tangential resection data formed in block 154, after a determination of NO in block 252, however, can transform or resect only that portion of the data near where a fiducial point should be located. For example, the transformation based on the N+1-fiducial point or N+1-fiducial marker subsets in block 240 can provide a selected transformation or correlation of the image space to the physical space. Because all of the fiducial markers have been found in the physical space in block 200, a determination of a position of a fiducial point in the image data can also be based on the transformation. Therefore, a determined or selected area of the image data can be used to form the resection data in block 154 after the determination of NO in block 252. Therefore, the point in the image data near the fiducial marker found in block 200 need only be searched. It will be understood, however, that any portion of the image data can be searched for additional fiducial point candidates. The fiducial point candidate determination process can then proceed as discussed above until either all of the fiducial points are found to match all of the fiducial markers or the user 60 stops the search.

Once all or a selected number of the fiducial markers 90 have been matched to fiducial points the registration in block 27 can be performed. The registration in block 27 registers the image space and the physical space. The registration, however, can occur after the user 60 touches or locates each of the fiducial markers that were imaged with the patient 32. The user 60 need not touch or identify in the image space any of the fiducial points. The process 20 allows for a system, such as the workstation 44, to identify all of the fiducial points or a selected number of the fiducial points in the image data and perform a registration of the image space to the physical space with the user 60 only determining the position of the fiducial markers in the physical space. The navigation system 30, therefore, can be efficiently implemented by a substantially single user step process. The user can register the image data of the physical space by only determining the position of the fiducial markers without being required to identify the fiducial points in the image data.

Further, as discussed above, the points identified in the image data can be any appropriate point on the fiducial marker 90. As discussed above the center point 108 of the fiducial marker 90 can be a selected point for performing the matching and transformation in the process 24. Nevertheless, any appropriate point, such as the edge, base point, or the like can be used in the registration process.

The description of the present teachings is merely exemplary in nature and, thus, variations that do not depart from the gist of the present teachings are intended to be within the scope of the present teachings. Such variations are not to be regarded as a departure from the spirit and scope of the present teachings.

What is claimed is:

1. A computer aided surgical navigation system to navigate a procedure relative to a physical space of a patient with registration of image space defined by image data to the physical space, comprising:
   a tracking system having a localizer and a tracking device;
   a plurality of fiducial markers operable to be associated with the patient and each of the plurality of fiducial markers defining a respective fiducial marker identification;
   an instrument associated with the tracking device, wherein the instrument includes a fiducial marker contact portion defining a single fiducial marker association point configured to contact each of the fiducial markers such that the tracking system is operable to track a location of the respective fiducial marker identification when the instrument is contacting each of the fiducial markers;
   a processor operable with the tracking system to determine a position of the single fiducial marker association point in the physical space;
   a memory system operable to store:
      the image data that defines the image space with a plurality of image points, wherein the plurality of image points has a plurality of fiducial points of the patient, wherein each of the fiducial points relate to the respective fiducial marker identification of each of the plurality of the fiducial markers, and
      a predetermined fiducial template that defines a configuration of the fiducial marker in the image data; and
   a display device operable to display the image data;
   wherein the processor is operable to execute a first set of instructions to compare the image data of the patient and the plurality of fiducial markers to the predetermined fiducial template to determine the fiducial points relating to the respective fiducial marker identification of at least selected ones of the fiducial markers in the image data including:
      comparing the predetermined fiducial template to the plurality of image points;
      determining the plurality of fiducial points from the plurality of image points based on the comparing the predetermined fiducial template;
   wherein the processor is further operable to execute a second set of instructions to match the determined plurality of fiducial points in image data that defines the image space to the respective fiducial marker identification in physical space including:
identifying a location of each of the respective fiducial marker identifications of the plurality of fiducial markers in the physical space based upon the tracked location of the instrument when contacting each of the fiducial markers;
matching a first subset of the plurality of fiducial points with a first subset of identified locations of each of the respective fiducial marker identifications of the plurality of fiducial markers;
calculating a transformation of the image space to the physical space based at least in part of the matching the first subset of the plurality of fiducial points with the first subset of identified locations of each of the respective fiducial marker identifications of the plurality of the fiducial markers; and
registering the image data that defines the image space to the physical space;
wherein the predetermined fiducial template includes at least one of a two dimensional template or a three dimensional template;
wherein the processor in executing the first set of instructions further includes:
forming a local 2D tangential resection of the acquired image data;
wherein comparing the predetermined template to the plurality of points includes comparing the two dimensional template to the local 2D tangential resection data.

2. The system of claim 1, further comprising:
a display device to display the registered image data and to display an icon representing a position of an instrument superimposed on the image data; and
a procedure instrument operable to be used in performing an image guided navigation procedure with the registered image data.

3. The system of claim 1, further comprising:
an imaging system to acquire the image data.

4. The system of claim 3, wherein the imaging system includes at least one of a magnetic resonance imaging system, an ultra sound imaging system, computed tomography imaging system, a X-ray imaging system, a PET imaging system, or a SPECT imaging system.

5. The system of claim 1, wherein the predetermined fiducial template of the fiducial marker stored in the memory system includes a computer readable template operable to be compared to the image data by executing the first set of instructions with the processor.

6. The system of claim 5, wherein the processor system in executing the first set of instructions when comparing the template to the plurality of points further includes systematically and virtually overlaying the predetermined fiducial template on the plurality of points in the image data and determining a match of the predetermined fiducial template to at least one of the plurality of points in the image data; and
wherein determining the sub-plurality of fiducial points includes:
determining a score of a comparison of the predetermined fiducial template to at least one of the plurality of points, wherein the score is based upon a determined match between the predetermined fiducial template and at least one of the plurality of points;
forming a list of candidate fiducial points based upon the determined sub-plurality of fiducial points and scoring each of the candidates and removing candidates from the list that do not have at least a threshold score; and
sorting the list of candidate fiducial points based upon the score including those only with the score at least as great as the threshold score.

7. The system of claim 1, wherein determining the sub-plurality of fiducial points includes determining an initial list of candidate fiducial points based upon comparing the two dimensional template to the formed 2D tangential resection data set.

8. The system of claim 7, wherein the processor in executing the first set of instructions further includes:
comparing the three dimensional template to the acquired image data at the location of the candidate fiducial points, wherein the acquired image data includes 3D image data;
determining a score for each of the comparisons made to the three dimensional template;
selecting the candidate fiducial points having the determined score above a stored threshold score; and
sorting the selected fiducial candidate points.

9. A computer aided surgical navigation system to navigate a procedure relative to a physical space of a patient with registration of image space defined by image data to the physical space, comprising:
a tracking system having a localizer and a tracking device;
a plurality of fiducial markers operable to be associated with the patient and each of the plurality of fiducial markers defining a respective fiducial marker identification;
an instrument associated with the tracking device, wherein the instrument includes a fiducial marker contact portion defining a single fiducial marker association point configured to contact each of the fiducial markers such that the tracking system is operable to track a location of the respective fiducial marker identification when the instrument is contacting each of the fiducial markers;
a processor operable with the tracking system to determine a position of the single fiducial marker association point in the physical space;
a memory system operable to store:
the image data that defines the image space with a plurality of image points, wherein the plurality of image points has a plurality of fiducial points of the patient, wherein each of the fiducial points relate to the respective fiducial marker identification of each of the plurality of the fiducial markers, and
a predetermined fiducial template that defines a configuration of the fiducial marker in the image data; and
a display device operable to display the image data;
wherein the processor is operable to execute a first set of instructions to compare the image data of the patient and the plurality of fiducial markers to the predetermined fiducial template to determine the fiducial points relating to the respective fiducial marker identification of at least selected ones of the fiducial markers in the image data including:
comparing the predetermined fiducial template to the plurality of image points;
determining the plurality of fiducial points from the plurality of image points based on the comparing the predetermined fiducial template;
wherein the processor is further operable to execute a second set of instructions to match the determined plurality of fiducial points in image data that defines the image space to the respective fiducial marker identification in physical space including:
  identifying a location of each of the respective fiducial marker identifications of the plurality of fiducial markers in the physical space based upon the tracked location of the instrument when contacting each of the fiducial markers;
  matching a first subset of the plurality of fiducial points with a first subset of identified locations of each of the respective fiducial marker identifications of the plurality of fiducial markers;
  calculating a transformation of the image space to the physical space based at least in part of the matching the first subset of the plurality of fiducial points with the first subset of identified locations of each of the respective fiducial marker identifications of the plurality of the fiducial markers; and
  registering the image data that defines the image space to the physical space;
wherein the processor in executing the second set of instructions further includes:
  determining at least N candidate fiducial points in the image data;
  wherein identifying the location of each of the plurality of fiducial markers includes identifying at least N fiducial markers;
  forming a N-fiducial point subset from the image data and producing a N-fiducial marker subset list from tracked locations of the instrument in the physical space;
  matching the N-fiducial point subset and the N-fiducial marker subset;
  wherein calculating a transformation includes calculating a first transformation based upon the matched N-fiducial point subset and the N-fiducial marker subset;
wherein the processor in executing the second set of instructions further includes:
  determining at least a N+1 candidate fiducial point;
  wherein identifying a plurality of locations of fiducial markers includes identifying at least a N+1 fiducial marker;
  determining whether the N+1 candidate fiducial point meets a stored match criterion when compared to the N+1 fiducial marker;
  forming a N+1-fiducial point subset with the N+1 candidate fiducial point and a N+1-fiducial marker subset with the N+1 fiducial marker if the match criterion is met between the N+1 candidate fiducial point and the N+1 fiducial marker.

10. The system of claim 9, wherein the processor system is further operable to execute instructions to calculate a transformation that includes determining a match for each of the determined plurality of fiducial points and identified locations of fiducial markers.

11. The system of claim 9, wherein the processor in executing the second set of instructions further includes:
  matching the N+1-fiducial point subset and the N+1-fiducial marker subset; and
  calculating a second transformation based upon the N+1-fiducial point subset and the N+1-fiducial marker subset.

12. The system of claim 11, wherein the processor in executing the second set of instructions further includes:
  determining whether the N+1-fiducial point subset includes all of the identified locations of fiducial markers.

13. The system of claim 12, wherein the processor in executing the second set of instructions further includes:
  identifying in the image data the position of identified locations of fiducial markers based upon the calculated transformation;
  comparing the template at the identified points;
  determining a second sub-plurality of fiducial points; and
  matching the second sub-plurality of the fiducial points to at least a sub-plurality of the identified fiducial markers.

14. The system of claim 13, wherein the processor in executing the second set of instructions further includes:
  registering the image space to the physical space based upon the identification of the fiducial points in the image data based upon the second determination of fiducial points.

15. A computer aided surgical navigation system to navigate a procedure relative to a physical space of a patient with registration of image space defined by image data to the physical space, comprising:
  a tracking system having a localizer and a tracking device;
  a plurality of fiducial markers operable to be associated with the patient and each of the plurality of fiducial markers defining a respective fiducial marker identification;
  an instrument associated with the tracking device, wherein the instrument includes a fiducial marker contact portion defining a single fiducial marker association point configured to contact each of the fiducial markers such that the tracking system is operable to track a location of the respective fiducial marker identification when the instrument is contacting each of the fiducial markers;
  a processor operable with the tracking system to determine a position of the single fiducial marker association point in the physical space;
  a memory system operable to store:
    the image data that defines the image space with a plurality of image points, wherein the plurality of image points has a plurality of fiducial points of the patient, wherein each of the fiducial points relate to the respective fiducial marker identification of each of the plurality of the fiducial markers, and
    a predetermined fiducial template that defines a configuration of the fiducial marker in the image data; and
  a display device operable to display the image data;
  wherein the processor is operable to execute a first set of instructions to compare the image data of the patient and the plurality of fiducial markers to the predetermined fiducial template to determine the fiducial points relating to the respective fiducial marker identification of at least selected ones of the fiducial markers in the image data including:
    comparing the predetermined fiducial template to the plurality of image points;
    determining the plurality of fiducial points from the plurality of image points based on the comparing the predetermined fiducial template;
  wherein the processor is further operable to execute a second set of instructions to match the determined plurality of fiducial points in image data that defines the image space to the respective fiducial marker identification in physical space including:
    identifying a location of each of the respective fiducial marker identifications of the plurality of fiducial markers in the physical space based upon the tracked location of the instrument when contacting each of the fiducial markers;

matching a first subset of the plurality of fiducial points with a first subset of identified locations of each of the respective fiducial marker identifications of the plurality of fiducial markers;

calculating a transformation of the image space to the physical space based at least in part of the matching the first subset of the plurality of fiducial points with the first subset of identified locations of each of the respective fiducial marker identifications of the plurality of the fiducial markers; and registering the image data that defines the image space to the physical space;

wherein the processor in executing the second set of instructions further includes:

determining at least N candidate fiducial points in the image data;

wherein identifying the location of the plurality of fiducial markers includes identifying at least N fiducial markers;

forming a N-fiducial point subset from the image data and producing a N-fiducial marker subset list from tracked locations of the instrument in the physical space;

matching the N-fiducial point subset and the N-fiducial marker subset;

wherein calculating a transformation includes calculating a first transformation based upon the matched N-fiducial point subset and the N-fiducial marker subset;

wherein the processor in executing the second set of instructions further includes:

determining a distance between each of the fiducial point candidates in the N-fiducial point subset; and determining a distance between each of the fiducial markers in the N-fiducial marker subset.

16. A computer aided surgical navigation system to navigate a procedure relative to a physical space of a patient with registration of image space defined by image data and the physical space, comprising:

a tracking system having a localizer and a tracking device;

a plurality of fiducial markers operable to be at least temporarily fixed to the patient and each of the plurality of fiducial markers defining a fiducial marker point;

an instrument associated with the tracking device, wherein the instrument includes a fiducial marker contact portion defining a single fiducial marker association point configured to contact each of the plurality of the fiducial markers in the physical space when at least temporarily fixed to the patient;

a processor operable with the tracking system to determine a position of the single fiducial marker association point in physical space at least based on the tracked location of the fiducial marker association point when contacting each of the plurality of fiducial markers at the fiducial marker point;

a memory system operable to store:

the image data that includes image data for both the patient and the plurality of fiducial markers, and a fiducial template configured to be compared to the image data of the plurality of fiducial markers to determine a fiducial point relating to each of the plurality of fiducial markers in the stored image data, wherein the fiducial template is at least one of a two dimensional computer readable fiducial template or a three dimensional computer readable fiducial template;

a display device operable to display the image data of at least the patient;

wherein the processor is operable to execute a first set of instructions to compare the image data of the fiducial marker to the fiducial template to determine at least a sub-plurality of the plurality of fiducial points in the image data relating to the plurality of fiducial markers, including:

comparing the two dimensional computer readable fiducial template to the image data;

determining a first list of fiducial point candidates based upon the comparison of the two dimensional computer readable fiducial template to the data;

determining a second list of fiducial point candidates including a score of the fiducial point candidates;

removing each of the fiducial point candidates from the second list that have a score less than a stored threshold score to form a refined second list;

wherein the processor is operable to execute a second set of instructions to match the fiducial points in image space defined by the image data to fiducial marker points determined in the physical space by tracking the instrument, including:

determining a plurality of N-fiducial point subsets from the refined second list of the fiducial point candidates; and determining a N-point fiducial marker subset from all of the determined positions of the fiducial markers based upon the tracked location of the instrument when contacting each of the plurality of fiducial markers at the fiducial marker point;

comparing each of the N-fiducial point subsets to each of the N-fiducial marker subsets;

determining a match between each of the compared N-fiducial point subsets and the N-fiducial marker subsets; and transforming the image space to the physical space based upon at least one match of the N-fiducial point subsets and the N-fiducial marker subsets.

17. The system of claim 16, wherein the processor is further operable to execute instructions to:

form a two dimensional resection of the image data;

wherein the fiducial template is at least the two dimensional computer readable fiducial template;

wherein the two dimensional computer readable fiducial template is compared to the two dimensional resected image data.

18. The system of claim 17, wherein the fiducial template is at least the three dimensional computer readable fiducial template;

wherein the first set of instructions executed by the processor further includes comparing the three dimensional computer readable fiducial template substantially more precisely to the fiducial marker association point in the image data identified to at least have the threshold score.

19. The system of claim 18, wherein the first set of instructions including comparing the three dimensional computer readable fiducial template substantially more precisely further includes:

determining an orientation, a position, or combinations thereof of the fiducial point candidate by matching it to the three dimensional computer readable fiducial template.

20. The system of claim 19, wherein the processor in executing the second set of instructions further includes:

determining at least one additional fiducial point match to a fiducial marker; and adding the additional point to at least one of the N-fiducial point subsets to form an N+1-fiducial point subset and adding at least one fiducial marker to the N-fiducial marker subset to create an N+1-fiducial marker subset.

21. The system of claim 19, wherein the processor in executing the second set of instructions further includes:
adding at least one fiducial point to the N-fiducial point subset and at least one fiducial marker to the N-fiducial marker subset until an identified fiducial point from the candidate list is not within a criterion when compared to the determined position of the fiducial marker.

22. The system of claim 21, wherein the criterion includes a distance, an angle, a geometry, or combinations thereof.

23. The system of claim 16, further comprising:
an imaging system selected from at least one of a magnetic resonance imaging system, a computed tomography imaging system, a X-ray imaging system, ultra sound imaging system, a PET imaging system, or a SPECT imaging system.

* * * * *